United States Patent [19]

Dubief et al.

[11] Patent Number: 5,160,730
[45] Date of Patent: Nov. 3, 1992

[54] USE OF AN AQUEOUS DISPERSION BASED ON ORGANOPOLYSILOXANES AND ON A CROSSLINKED AMMONIUM ACRYLATE/ACRYLAMIDE COMPOLYMER IN COSMETICS, FOR THE TREATMENT OF HAIR OR THE SKIN AND/OR IN DERMATOLOGY

[75] Inventors: Claude Dubief, Le Chesnay; Daniele Cauwet, Paris, both of France

[73] Assignee: L'Oreal, France

[21] Appl. No.: 599,611

[22] Filed: Oct. 18, 1990

[30] Foreign Application Priority Data

Oct. 20, 1989 [FR] France ................ 89 13787

[51] Int. Cl.$^5$ .................. A61K 7/42; A61K 7/075
[52] U.S. Cl. ................................. 424/59; 424/70
[58] Field of Search ................. 424/487, 59, 70

[56] References Cited

U.S. PATENT DOCUMENTS 4,883,659 11/1989 Goodman et al. .......... 514/844
4,983,383 1/1991 Maksimoski et al. ........ 424/70

FOREIGN PATENT DOCUMENTS 0042678 12/1981 European Pat. Off. .
0116207 8/1984 European Pat. Off. .
0173033 3/1986 European Pat. Off. .
0260641 3/1988 European Pat. Off. .
2014584 8/1979 United Kingdom .

OTHER PUBLICATIONS

*Chemical Abstracts*, vol. 99, No. 16, Oct., 1983; p. 342, "Cosmetic Creams and Lotions", Abstract #99:128,150k.

Primary Examiner—Richard L. Raymond
Assistant Examiner—S. Mark Clardy
Attorney, Agent, or Firm—Marshall, O'Toole, Gerstein, Murray & Bicknell

[57] ABSTRACT

The present invention relates to the use of an aqueous dispersion containing at least an organopolysiloxane and a crosslinked ammonium acrylate/acrylamide copolymer in a cosmetically acceptable aqueous medium in cosmetics for the treatment of hair or of the skin and/or in dermatology.

22 Claims, No Drawings

USE OF AN AQUEOUS DISPERSION BASED ON ORGANOPOLYSILOXANES AND ON A CROSSLINKED AMMONIUM ACRYLATE/ACRYLAMIDE COMPOLYMER IN COSMETICS, FOR THE TREATMENT OF HAIR OR THE SKIN AND/OR IN DERMATOLOGY

The invention relates to the use of an aqueous dispersion based on organopolysiloxanes and on a cross-linked ammonium acrylate/acrylamide polymer in cosmetics, for the treatment of hair or the skin and/or in dermatology.

Silicone oils are already employed in cosmetics as lubricant in compositions for treating hair or the skin. They are mainly polydimethylsiloxanes.

Cationic polymers or surfactants have been employed for a long time in order to impart softness to hair or the skin, or else to make hair easier to disentangle. The cationic compounds have the disadvantage, after repeated applications, of weighing down the head of hair, giving it an oily appearance or of producing a sticky effect on the skin.

The Applicant has found, surprisingly, that the use of an aqueous dispersion based on organopolysiloxanes and on a crosslinked ammonium acrylate/acrylamide copolymer for the treatment of hair makes it possible to obtain gleaming, silky and light hair whose disentangling and softness properties are appreciably improved.

The use of this aqueous dispersion in the treatment of the skin also makes it possible to impart a soft feel to the latter without any sticky effect.

The aqueous dispersions employed in cosmetics or dermatology, according to the present invention, spread much more easily on the skin and on hair than the compositions of the prior art based on cationic compounds.

The Applicant has also found that the cosmetic compositions in the form of aqueous dispersion, according to the present invention, were remarkably stable, that their cosmetic properties were retained even after a number of successive applications and more particularly in an unrinsed application to hair.

A subject of the invention consists therefore of the use of an aqueous dispersion containing at least one organopolysiloxane and a crosslinked ammonium acrylate/acrylamide copolymer in the cosmetic treatment of hair or of the skin and/or dermatological treatment.

Another subject of the invention concerns cosmetic or dermatological compositions for the treatment of hair or of the skin, in the form of aqueous dispersions.

Another subject of the invention concerns processes for the cosmetic treatment of hair or of the skin, employing these compositions, according to the desired application.

Other subjects of the invention will become apparent in the light of the description and of the examples which follow.

The main subject of the present invention is the use of an aqueous dispersion for the cosmetic treatment of hair or of the skin and/or dermatological treatment, characterized in that the said dispersion contains an organopolysiloxane and a crosslinked ammonium acrylate/acrylamide copolymer at least in a cosmetically or physiologically acceptable medium.

The organopolysiloxanes employed in the dispersions according to the present invention are organopolysiloxane oils or organic solutions of organosiloxane gum or resin.

Among the organosiloxanes employed in accordance with the present invention there may be mentioned, no limitation being implied:

I. VOLATILE SILICONES

These have a boiling point of between 60° C. and 260° C. Among silicones of this type there are mentioned:

(i) cyclic silicones containing 2 to 7 and preferably 4 to 5 silicon atoms. These are, for example, the octamethylcyclotetrasiloxane sold under the name Volatile Silicone 7207 by Union Carbide or Silbione 70045 V2 by Rhône Poulenc, the decamethylcyclopentasiloxane sold under the name of Volatile Silicone 7158 by Union Carbide, Silbione 70045 V5 by Rhône Poulenc, and mixtures thereof.

Also mentioned are the cyclocopolymers of the dimethylsiloxane/methylalkylsiloxane type, such as Silicone Volatile FZ 3109 sold by Union Carbide, of chemical structure:

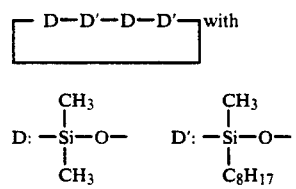

(ii) linear volatile silicones containing 3 to 9 silicon atoms and possessing a viscosity lower than or equal to 5 cSt at 25° C. These are, for example, the hexamethyldisiloxane sold under the name Silbione 70 041 V 0.65 by Rhône Poulenc. This type of product is described in the article by Todd & Byers "Volatile silicone fluids for cosmetics", Cosmetics and Toiletries, Vol. 91, Jan 76, p. 27-32.

II. Nonvolatile Silicones

These consist chiefly of polyalkylsiloxanes, polyarylsiloxanes, polyalkylarylsiloxanes, modified or unmodified polyethersiloxane copolymers, silicone gums and resins and organomodified polysiloxanes, and mixtures thereof.

Among the polyalkylsiloxanes there may be chiefly mentioned linear polydimethylsiloxanes with trimethylsilyl end groups with a viscosity of 5 to 2,500,000 cSt at 25° C. and preferably 10 to 1,000,000 cSt such as, for example, and without any limitation being implied:

the Silbione oils of the 70 047 and 47 series marketed by Rhône Poulenc, like the 47 V 500,000 or 70 047 V 300 oil from Rhône Poulenc, the oils of the 200 series from Dow Corning, the Viscasils from General Electric;

and some oils from the SF series from General Electric (SF 96, SF 18).

Also mentioned are linear polydimethylsiloxanes with trihydroxysilyl end groups, such as the oils of the 48 V series from Rhône Poulenc.

In this class of polyalkylsiloxanes there may also be mentioned the polyalkylsiloxanes sold by Goldschmidt under the names Abilwax 9800 and Abilwax 9801, which are polyalkyl($C_1$-$C_{20}$)siloxanes.

Among the polyalkylarylsiloxanes there may be mentioned linear and/or branched polydimethylphenylsiloxanes and polydimethyldiphenylsiloxanes, with a viscosity of 10 to 50,000 cSt at 25° C., such as, for example:

the Rhodorsil 763 oil from Rhône Poulenc, the Silbione 70 641 oils from Rhône Poulenc, such as the Silbione 70 641 V 30 and 70 641 V 200 oil, the product DC 556 Cosmetic Grade Fluid from Dow Corning, the AB12 AV 1000 oil from Goldschmidt, the silicones of the PK series from Bayer, such as PK20, the silicones of the PN and PH series from Bayer, such as PN 1000 and PH 1000, some oils of the SF series from General Electric, such as SF 1250, SF 1265, SF 1154 and SF 1023.

Among the modified or unmodified polyethersiloxane copolymers there may be mentioned copolymers of propylene and/or ethylene oxide with a diorganosiloxane, such as, for example the dimethicone copolyols sold by Dow Corning under the name DC 1248 and the alkyl($C_{12}$)methicone copolyol sold by Dow Corning under the name Q2 5200.

The Silwet grades L 77, L 711, L 722 and L 7500, sold by Union Carbide may also be mentioned.

The silicone gums in accordance with the present invention are polydiorganosiloxanes of high molecular mass of between 200,000 and 1,000,000, employed by themselves or as a mixture in a solvent chosen from volatile silicones, polydimethylsiloxane (PDMS) oils, polyphenylmethylsiloxane (PPMS) oils, isoparaffins, methylene chloride, pentane, dodecane, tridecane, tetradecane or mixtures thereof.

For example, the following compounds are mentioned:

poly[(dimethylsiloxane)/(methylvinylsiloxane)],
poly[(dimethylsiloxane)/(diphenylsiloxane)],
poly[(dimethylsiloxane)/(phenylmethylsiloxane)],
poly[(dimethylsiloxane)/diphenylsiloxane)/(methylvinylsiloxane)].

For example, the following mixtures may be mentioned, no limitation being implied:

1) the mixtures made from a polydimethylsiloxane hydroxylated at a chain end (Dimethiconol according to the CTFA nomenclature), and from a cyclic polydimethylsiloxane (Cyclomethicone according to the CTFA nomenclature), such as the product Q2 1401 sold by Dow Corning;

2) the mixtures made from a polydimethylsiloxane gum with a cyclic silicone, such as the product SF 1214 Silicone Fluid from General Electric, which is an SE 30 gum of MW 500,000 solubilized in SF 1202 Silicone Fluid (decamethylcyclopentasiloxane);

3) the mixtures of two PDMSs of different viscosities, especially of a PDMS gum and of a PDMS oil, such as the products SF 1236 and CF 1241 from General Electric. The product SF 1236 is the mixture of an SE 30 gum defined above with a viscosity of 20 m$^2$/s and of an SF 96 oil with a viscosity of $5 \times 10^{-6}$ m$^2$/s (15% of SE 30 gum and 85% of SF 96 oil). The product CF 1231 is the mixture of an SE 30 gum (33%) and of a PDMS (67%) which has a viscosity of $10^{-3}$ m$^2$/s:

4) the mixtures of a polydimethylsiloxane containing polyoxyethylenated or polyoxypropylenated side chains (Dimethicone Copolyol) with a cyclic polydimethylsiloxane (Cyclomethicone), such as the product Q2 3225 C from Dow Corning.

The organopolysiloxane resins capable of being employed in accordance with the invention are crosslinked siloxane systems containing the units: $R_2SiO_{2/2}$, $RSiO_{3/2}$ and $SiO_{4/2}$, in which R denotes a hydrocarbon group containing 1 to 6 carbon atoms or a phenyl group Among these products, those particularly preferred are those in which R denotes a lower alkyl radical or a phenyl radical.

Among these resins there may be mentioned the product sold under the name Dow Corning 593 and the Silicones Fluid SS 4230 and SS 4267 from General Electric (dimethyl/trimethylpolysiloxane).

The organomodified silicones, in accordance with the present invention, are silicones such as defined above, whose general structure includes one or more organofunctional groups attached directly to the siloxane chain or attached through the intermediacy of a hydrocarbon radical.

There are mentioned, for example, silicones containing:

a. substituted or unsubstituted amine groups, as in the GP4 Silicone Fluid from Genesee, GP 7100 from Genesee, Q2 8220 and DC 929 from Dow Corning, and AFL 40 from Union Carbide;

b. thiol groups, as in GP 72 A and GP 71 silicones from Genesee;

c. carboxylate groups, such as the product described in European Patent EP 186,507 of Chisso Corporation;

d. hydroxyl groups, such as the polyorganosiloxanes containing a hydroxyalkyl functional group, which are described in French Patent Application No. FR-85/16,334, corresponding to the following formula:

$$(R_1)_3-Si-\left[O-\underset{\underset{OH}{\overset{R'_1}{|}}}{\overset{R_1}{\underset{|}{Si}}}\right]_p \left[O-Si(R_1)_2\right]_q O-Si(R_1)_3 \quad (I)$$

in which:

the radicals $R_1$, which are identical or different, are chosen from methyl and phenyl radicals, at least 60 mol % of the radicals R being methyl;

the radical $R'_1$ is a $C_2$-$C_{18}$ divalent alkylene hydrocarbon chain unit;

p is between 1 and 30 inclusive q is between 1 and 150 inclusive;

e. alkoxylated groups, as in the Silicone copolymer F 755 from SWS Silicones and the products Abilwax 2428, Abilwax 2434, Abilwax 2440 from Goldschmidt;

f. acyloxyalkyl groups, such as, for example, the polyorganopolysiloxanes described in French Patent Application No. 88/17,433, corresponding to the following formula:

$$(R_2)_3Si\left[O-\underset{\underset{OCOR''}{\overset{R'_2}{|}}}{\overset{R'_2}{\underset{|}{Si}}}\right]_p \left[O-\underset{\underset{OH}{\overset{R'_2}{|}}}{\overset{R'_2}{\underset{|}{Si}}}\right]_q \left[O-\underset{\overset{R'_2}{|}}{\overset{R'_2}{\underset{|}{Si}}}\right]_r OSi(R_2)_3 \quad (II)$$

in which:

$R_2$ denotes methyl, phenyl, —COOR″, hydroxyl, only one of the $R_2$ per silicon atom may be OH;

$R'_2$ denotes methyl, phenyl, at least 60 mol % of the set of the radicals $R_2$ and $R'_2$ are methyl;

R″ denotes $C_8$-$C_{20}$ alkyl or alkenyl;

R denotes a linear or branched $C_2$–$C_{18}$ divalent alkylene hydrocarbon;

r is between 1 and 120 inclusive;

p is between 1 and 30;

q has the value of 0 or is smaller than 0.5 p, p+q being between 1 and 30; the polyorganosiloxanes of formula (II) may contain

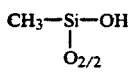

groups in proportions not exceeding 15% of the sum p+q+r.

These compounds of formula (II) can be prepared by esterification of the polyorganosiloxanes containing a hydroxyalkyl functional group of formula (I) above.

The esterification is performed in a known manner, with an acid R"COOH or the acid anhydride, at a temperature of between 100° and 250° C. in the optional presence of a catalyst like aluminium chloride or zinc chloride or of a strong acid like hydrochloric acid or sulphuric acid.

A transesterification can also be performed by heating a methyl ester of formula R"COOCH$_3$ and a diorganopolysiloxane of formula (I) to 100°–150° C. in the presence of an acidic catalyst like para-toluenesulphonic acid or an acidic earth of the montmorillonite type (Katalysator KSF/O, sold by Süd-Chemie - A. G. München);

g. diester groups, and especially dimethyl itaconate, such as the oils containing a dimethyl itaconate functional group which are described in Luxembourgian Patent Application No. 87/350 by the Applicant, corresponding to the following formula:

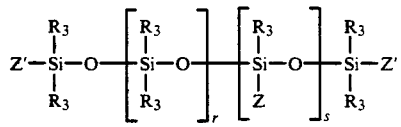

in which:

the radicals R$_3$, which are identical or different, denote a $C_1$–$C_{20}$ alkyl, vinyl, phenyl, 3,3,3-trifluoropropyl or hydroxyl, provided that only one radical R$_3$ may denote OH per silicon atom;

the symbols Z', which are identical or different, denote R$_3$ or Z;

Z is chosen from the groups:

—CH$_2$—CH—(COOR'$_3$)—CH$_2$—COOR'$_3$

—C(CH$_3$)(COOR'$_3$)—CH$_2$—COOR'$_3$

R'$_3$ denotes a saturated monovalent $C_1$–$C_{12}$ hydrocarbon radical, a monovalent $C_2$–$C_{12}$ alkoxyalkyl radical, or a $C_6$–$C_{12}$ aryl, aralkyl or alkylaryl radical;

r is between 0 and 500 inclusive;

s is between 0 and 50 inclusive;

if s is equal to 0, one of the symbols Z' has the value Z.

These compounds can be prepared according to the following procedures.

During a first stage (A$_1$) an organic diester of formula:

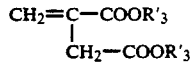 (IIIA)

R'$_3$ having the same meaning as in formula (III), is added to a hydroorganosilane of formula:

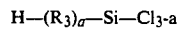 (IIIB)

R$_3$ having the same meaning as in formula (III) above and a being equal to 0, 1 or 2.

An addition product is thus obtained, of formula:

 (IIIC)

in which R$_3$, Z and a have the meanings shown above.

Stage (A$_1$) may be performed in bulk or in solution in an organic solvent.

The reaction is exothermic. The operation is generally carried out under reflux of the reaction mixture at a temperature of between 60° C. and 140° C. over a period of between 10 minutes and 3 hours.

The silane of formula (IIIB) may be run into the diester of formula (IIIA) or vice-versa, or at the same time.

It is preferable to employ a molar excess (of 10 to 50%) of silane of formula (IIIB).

The operation is carried out in the presence of a catalyst, with a view to enhancing the reaction kinetics. The catalyst which may be employed are those employed for producing the hydrosilylation reactions; those which may be employed are therefore in particular organic peroxides, UV radiation and catalysts based on a metal of the platinum group, in particular platinum, ruthenium and rhodium in a quantity of 10 to 500 ppm (calculated as the weight of metal) relative to the weight of silane of formula (IIIB).

At the end of reaction, the volatile products are removed by vacuum distillation. A water pump vacuum of 0.1 to 3 kPa is generally sufficient.

During a second stage (A$_2$) the hydrolysis (or the cohydrolysis) and the polycondensation of a silane of formula (IIIC) is performed.

This hydrolysis or cohydrolysis and polycondensation may be preferably carried out in a liquid aqueous phase in an acidic medium (preferably HCl) or in a basic medium (preferably NH$_4$OH) or in a solvent medium, in conditions which are similar to those of the hydrolysis of chlorosilanes, such as described on pages 193 to 200 of Noll's work "Chemistry and Technology of Silicones", Academic Press (1968).

The concentration of acid or of base in the water is generally between 10 and 30% by weight. The hydrolysis medium always contains at least 2 moles of water per mole of silane, generally from 10 to 100 moles of water. The hydrolysis may be performed continuously or noncontinuously at room temperature (20° C.) or at a temperature of between 5° and 90° C. The hydrolysis may be performed at a pressure equal to or higher than atmospheric pressure, continuously or noncontinuously with reinjection of water, at least in the case of the continuous process, in order to maintain a constant aqueous phase.

With a view to obtaining the polymers of formula (III) or mixtures thereof, the silanes of formula (IIIC) in which a=1 are hydrolysed and polycondensed in the optional presence of a dichlorodiorganosiloxane of formula:

 (IIID)

in which $R_3$ has the definition given in formula (III) above.

The polycondensation can be stopped merely by neutralizing the reaction mixture. In this case the polymers of formula (III) which are obtained are blocked at each of their ends by a hydroxyl group (silanol) or by the unit $(R_3)_2SiO_{0.5}$ if the silane $(R_3)_2ZSiCl$ is employed.

The polycondensation can also be stopped by adding an organosilicon compound capable of reacting with the hydroxyl ends.

The duration of the hydrolysis may be between a few seconds and several hours.

After hydrolysis the aqueous phase is separated from the siloxane phase by any suitable physical means, generally by density separation and extraction with an organic solvent such as isopropyl ether.

To prepare the polymers of formula (III) it is also possible, according to a second process (B), to start with the corresponding polymer in which all the radicals Z and optionally Z' are hydrogen atoms and to add a diester of formula (IIIA) above using a hydrosilylation reaction.

As in stage ($A_1$) of process (A), process (B) makes use of an analogous hydrosilylation reaction and it is desirable to perform this reaction with the same catalysts as those indicated in stage ($A_1$).

This reaction may be carried out in bulk or in an organic solvent at a temperature between ordinary temperature (25° C.) and 170° C.

At the end of reaction the volatile products are removed by vacuum distillation and/or by extraction;

h. quaternary ammonium groups, as in the products X2 81 08 and X2 81 09, and the product Abil K 3270 from Goldschmidt;

i. amphoteric or betainic groups, such as in the product sold by Goldschmidt under the name Abil B 9950;

j. anionic groups of carboxylic type, such as the alkylcarboxylic groups like those present in the product X-22-370/E from Shin-Etsu, 2-hydroxyalkylsulphonate and 2-hydroxyalkylthiosulphate, such as the products sold by Goldschmidt under the names "Abil S 201" and "Abil S 225".

The polyorganosiloxanes which are particularly preferred according to the present invention are chosen from:

1) cyclic volatile silicones, such as octamethylcyclotetrasiloxane and decamethylcyclopentasiloxane;

2) nonvolatile silicones of the linear polyalkylsiloxane type with trimethylsilyl end groups, such as the Silbione 70047 and 47 oils, such as the oil 47 V 500,000, marketed by Rhône Poulenc, or of the polyalkylarylsiloxane type, such as the Silbione 70641V200 oil marketed by Rhône Poulenc;

3) mixtures of organosiloxanes and of cyclic silicones such as Q2 1401 from Dow Corning and SF 1214 Silicone Fluid from General Electric;

4) the (dimethyl/trimethylpolysiloxane)resin sold under the name of Dow Corning 593 by Dow Corning;

5) organomodified polyorganosiloxanes chosen from PDMS oils containing a hydroxypropyl functional group of formula (I) such as defined above, in which $R_1$ denotes methyl and $R'_1$ a trimethylene or 2-methyltrimethylene group; PDMS oils containing an acyloxyalkyl group of formula (II) such as defined above, in which $R_2$ and $R'_2$ denote a methyl radical, R" denotes a mixture of $C_{16}H_{33}$ and $C_{18}H_{37}$ radicals and R denotes a trimethylene or a 2-methyltrimethylene; and oils containing a dimethyl itaconate group, corresponding to the formula (III) defined above, in which $R_3$ denotes $CH_3$ and Z' denotes OH.

The polyorganosiloxanes employed in accordance with the present invention are present in the aqueous dispersion in a proportion of between 0.5 and 50% by weight and preferably between 1 and 30% by weight, relative to the total weight of the dispersion.

The crosslinked ammonium acrylate/acrylamide copolymer employed in accordance with the present invention is more particularly an ammonium acrylate/acrylamide (95/5 by weight) copolymer crosslinked with a compound containing olefinic polyunsaturation, such as divinylbenzene, tetraallyloxyethane, diallyl ether, or polyallylpolyglyceryl ethers or the allyl ethers of alcohols from the sugar series, such as erythritol, pentaerythritol, arabitol, mannitol, sorbitol or glucose.

Analogous copolymers are described and prepared in French Patent FR-2,416,723 (Hoechst).

Other processes for obtaining a copolymer of this type are also described in U.S. Pat. No. 2,798,053 and U.S. Pat. No. 2,923,692.

The crosslinked ammonium acrylate/acrylamide copolymer is present in the aqueous dispersions according to the invention in proportions of between 0.1 and 10% by weight and preferably between 0.1 and 4% by weight relative to the total weight of the dispersions.

A preferred form of employing the aqueous dispersion in cosmetics or dermatology according to the present invention consists in using a dispersion containing, in a cosmetically or physiologically acceptable aqueous medium:

a) an organopolysiloxane;

b) a crosslinked ammonium acrylate/acrylamide copolymer;

c) a nonionic emulsifying agent;

d) a mineral oil.

The mineral oil employed according to the present invention is a mixture of hydrocarbons distilling between 250° C. and 300° C., obtained in the refining of crude oil. Liquid paraffin is preferably employed. The oil is present in the dispersions employed according to the invention in proportions of between 0.08 and 6.5% by weight and preferably between 0.08 and 2.5% by weight relative to the total weight of the dispersions.

The nonionic emulsifying agents employed in the present invention are preferably chosen from oil-soluble surfactants which have a hydrophile/lipophile ratio (or HLB) lower than 7.

A mixture of sorbitan stearate and of a hydrophilic ethoxylated derivative is preferably employed as nonionic emulsifying agent.

In the dispersions employed according to the invention the emulsifying agent is present in proportions of between 0.01 and 1% by weight and preferably between 0.1 and 0.6% by weight.

A particularly preferred form of aqueous dispersion employed according to the invention contains the ammonium acrylate/acrylamide (95/5 by weight) copolymer crosslinked with a crosslinking agent containing olefinic polyunsaturation, dispersed in a water-in-oil emulsion consisting of 30% by weight of the said polymer, 25% by weight of paraffin, 4% of a mixture of sorbitan stearate and of hydrophilic ethoxylated derivative and 41% by weight of water. Such an emulsion is marketed under the name of PAS 5161 by Hoechst.

This particular aqueous dispersion, employed according to the invention, is preferably prepared simply by mixing the organosiloxane polymer with the emulsion defined above at room temperature and with stirring. The mixture thus obtained can be introduced directly into water containing other ingredients chosen depending on the desired application.

The water-in-oil emulsion containing the cross-linked ammonium acrylate/acrylamide (95/5 by weight) copolymer is preferably present in the aqueous dispersion in proportions such that the concentration of copolymer is between 0.05 and 10% by weight and preferably between 0.1 and 5% by weight of copolymer active substance, relative to the total weight of the dispersion.

Another subject of the invention consists of a composition in the form of aqueous dispersion intended for the treatment of hair or the skin in cosmetics and/or in dermatology, characterized in that the aqueous dispersion is such as defined above.

The compositions in accordance with the present invention may additionally contain adjuvants usually employed in cosmetics, such as perfumes, colorants, preserving agents, sequestering agents, vegetable, animal or synthetic oils, sunscreens, anionic, nonionic, amphoteric or cationic surface-active agents, polymers, conditioning agents, foam stabilizers, propellants, or other adjuvants usually employed in compositions for hair or the skin, according to the envisaged application.

The cosmetic compositions intended for the treatment of hair, in accordance with the invention, may be employed in particular as a shampoo, as a rinsing product, to be applied before or after shampooing, before or after dyeing or bleaching, before or after permanent waving or straightening or as an unrinsed styling product, such as in hair setting or blow-drying lotions.

The cosmetic compositions in accordance with the present invention which are intended for skin treatment and care may be in the form of a product for the bath or shower, of a suntanning product, of a product for shaving, of perfumed lotion, cream or milk for skin care or of antisolar compositions.

The compositions in accordance with the present invention can be applied in dermatology. They contain, in an effective quantity, a substance which is active from a dermatological viewpoint, such as, for example, vitamin A, carotenoids, proteins, natural pigments, retinoids, depigmenting agents, antiseborrhoeic or antiacne substances and antiinflammatory agents.

The cosmetic or dermatological compositions according to the present invention have a pH of between 3 and 10 and preferably between 5 and 7. This pH can be adjusted using alkalifying or acidifying agents usually employed in cosmetics and in dermatology.

A process for the cosmetic treatment of hair according to the invention consists in applying compositions such as defined above to hair according to the intended usage (shampoo, rinsing treatment, styling treatment without rinsing), without any need for an application time to be adhered to.

A process for a cosmetic treatment of the skin according to the invention consists in applying to the latter a composition such as defined above, according to the intended use (bath, shower, suntanning products, products for shaving, perfumed lotions, or treatment creams or milks).

The examples which follow are intended to illustrate the present invention without, however, being limiting in nature.

REFERENCE EXAMPLE 1

Preparation of a silane of formula (IIIC), in which:
$R_3$ denotes $CH_3$
a denotes 1
Z is a mixture of radicals
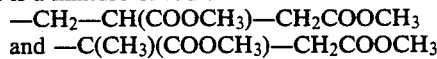
907 g, that is 5.74 moles of methyl itaconate and 129 mg of chloroplatinic acid ($H_2PtCl_6$) are charged into a 2-liter three-necked reactor fitted with a condenser, a stirrer and a dropping funnel The temperature is raised to 116° C. and 792.5 g (6.89 moles) of $CH_3HSiCl_2$ are then run in over 65 minutes, that is a 20% molar excess relative to the itaconate. Since the reaction is exothermic, the temperature remains in the region of 120° C. without any additional heat input. At the end of addition the temperature is 112° C. The reaction mixture is kept refluxing for 1 hour 50 minutes and the excess $CH_3HSiCl_2$ is then distilled off and 1,274 g of a liquid adduct whose boiling point is 80° C. at 0.13 kPa are obtained The weight yield of adduct is 71%.

NMR analysis of the adduct shows that it contains approximately 60 mol % of radicals
—$(CH_2)$—$CH(COOCH_3)$—$CH_2$—$COOCH_3$
and 40 mol % of unit —$C(CH_3)(COOCH_3)$—$CH_2$—$COOCH_3$.

REFERENCE EXAMPLE 2

Preparation of a compound of formula (III), in which:
$R_3$ denotes $CH_3$;
$Z'$ denotes OH;
Z is a mixture of radicals:
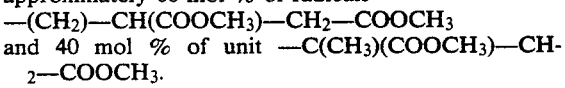
r denotes a mean statistical value equal to 40;
s denotes a mean statistical value equal to 2.

2,800 g of water are charged into a 10-liter three-necked reactor, into which 903 g (7 moles) of $(CH_3)_2SiCl_2$ and 98 g (0.35 moles) of the adduct obtained in Reference Example 1 are run in over one hour. During the addition the temperature gradually rises from 25° to 65° C. After the addition the reaction mixture is kept stirred for 30 minutes and the acidic liquors are separated off. 350 ml of isopropyl ether are added, three washings are performed and the ether solution is concentrated in a first stage up to 100° C. at atmospheric pressure and then up to 80° C. under a vacuum of 2.5 kPa.

456 g of clear and colourless oil are then obtained, which has the following characteristics:

| | |
|---|---|
| viscosity at 25° C. | 20 mPa s |
| % of hydroxyl (by weight) | 1% |
| % of ester functional group (by weight) | 4.8% |
| weight yield of oil | 77% |

REFERENCE EXAMPLE 3

Preparation of a compound of average formula (II) in which:
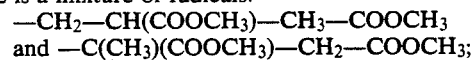
p=7.9
q=1.4
r=9.3

$R'' =$ mixture of $C_{16}H_{33}$ and $C_{18}H_{37}$ radicals.

This compound contains on average approximately two $$\begin{array}{c} CH_3SiOH \\ | \\ O_{2/2} \end{array}$$

units

Into a 3-liter three-necked round bottom flask equipped with a stirrer, fitted with a heating device, a reflux condenser and purged by a stream of nitrogen by bubbling into the reaction mixture, are charged 800 g of polydimethylsiloxane oil containing a γ-hydroxypropylated functional group (obtained by a reaction of hydrosilylation of allyl alcohol with a polydimethylpolymethylhydrosiloxane oil in the presence of a platinum catalyst) of average structure, determined by $^{29}$Si NMR analysis, corresponding to the average formula (I), in which:

$R_1 = CH_3$.
$R'_1 = -(CH_2)_3-$
$p = 6.8$
$q = 6.8$
and containing on average one $$\begin{array}{c} CH_3-Si-OH \\ | \\ O_{2/2} \end{array}$$

unit determined by titration to contain 459.5 meq/100 g of propyl alcohol functional group, and 1,207 g of a $R''CO_2Me$ fatty ester cut ($R''$ having the composition:

| | |
|---|---|
| $C_{14}H_{29}$ | 0.5 |
| $C_{16}H_{33}$ | 37.0 |
| $C_{18}H_{37}$ | 61.0 |
| $C_{20}H_{41}$ | 1.5 |
| | 100% by weight |

The mixture is raised to 120° C. by heating. When the temperature is reached, 6.02 g of paratoluenesulphonic acid monohydrate ($CH_3C_6H_4SO_3H.H_2O$) are added.

The reaction is carried out with stirring for 17 hours. At the end of the reaction 500 ml of hexane are added to the reaction mixture and the removal of the acidic catalyst is then performed by washing and neutralization with aqueous $NaHCO_3$.

The hexane phase is dried over $Na_2SO_4$ and is filtered. 1,822.6 g of a clear amber-coloured oil in which 85% of the alcohol functional groups are converted into fatty ester functional groups are obtained after removal of the hexane by distillation at 110° C. at 1.33 kPa for 3 hours. The oil assumes the appearance of a wax on cooling to room temperature.

$^{29}$Si NMR analysis shows the structure referred to above.

The residual content of propyl alcohol functional group is 37 meq/100 g and of methyl $C_{16}+C_{18}$ fatty esters 20% by weight.

EXAMPLE 1

A conditioner composition, not to be rinsed off, is prepared, which is in the form of a fluid gel, whose formulation is as follows:

| | |
|---|---|
| Crosslinked ammonium acrylate/acrylamide copolymer emulsion, sold under the name PAS 5161 by Hoechst | 0.50 g AS as copolymer |
| Hydroxypropylated polyorganosiloxane of formula: | |

$$(CH_3)_3Si-\left[O-\underset{\underset{OH}{|}}{\underset{|}{\overset{CH_3}{\overset{|}{Si}}}}-(CH_2)_3\right]_{1.5}\left[O-\underset{\underset{CH_3}{|}}{\overset{CH_3}{\overset{|}{Si}}}\right]_{115}O-Si(CH_3)_3 \quad 10.0\text{ g}$$

$(Mn \simeq 9,000)$

| | |
|---|---|
| N-(1,3-bis-hydroxymethyl)-2,5-dioxo-4-imidazolidinyl urea sold by Sutton under the name Germall II | 0.1 g |
| water q.s. | 100.0 g | spontaneous pH: 6.25

This composition is applied to washed and roughly dried hair. No rinsing is carried out and the hair is dried. The wet and dried hair disentangles remarkably well. The dried hair is soft and gleaming.

EXAMPLE 2

A cream for the care of damaged hair, not to be rinsed off, is prepared, whose composition is as follows:

| | |
|---|---|
| Crosslinked ammonium acrylate/acrylamide copolymer emulsion, sold under the name PAS 5161 by Hoechst | 1.0 g AS as copolymer |
| Polyorganosiloxane containing an acyloxypropyl functional group of formula: | |

$$(R_2)_3Si-(O-\underset{\underset{OCOR''}{|}}{\overset{R'_2}{\overset{|}{Si}}})_p-(O-\underset{\underset{OH}{|}}{\overset{R'_2}{\overset{|}{Si}}})_q-(O-\underset{\underset{R'_2}{|}}{\overset{R'_2}{\overset{|}{Si}}})_r-OSi(R_2)_3 \quad 5.0\text{ g}$$

in which:
$R_2 = R'_2 = CH_3$, $R = (CH_2)_3$
$p = 7.9$
$q = 1.4$
$r = 9.3$
$R'' =$ mixture of $C_{16}H_{33}$ and $C_{18}H_{37}$ radicals.

This compound contains on average about two $$\begin{array}{c} CH_3SiOH \\ | \\ O_{2/2} \end{array}$$

units prepared according to Reference Example 3

| | |
|---|---|
| N-(1,3-bis-hydroxymethyl)-2,5-dioxo-4-imidazolidinylurea sold by Sutton under the name Germall II | 0.1 g |
| water q.s. | 100.0 g |
| spontaneous pH: 6 | |

This oily cream is applied to washed and roughly dried hair. It improves the disentangling of wet and dried hair and makes dried hair soft and smooth.

EXAMPLE 3

A treatment milk, not to be rinsed off, is prepared, which can be applied as a conditioner to clean and wet hair or as a finishing treatment on dried hair, whose composition is as follows:

| | |
|---|---|
| Crosslinked ammonium acrylate/acrylamide copolymer emulsion, sold under the name PAS 5161 by Hoechst | 0.25 g AS as copolymer |
| Polydimethyldiphenylsiloxane sold by Rhône Poulenc under the name Silbione 70641 V 200 oil | 0.5 g |
| N-(1,3-bis-hyroxymethyl)-2,5-dioxo-4-imidazolidinylurea sold by Sutton under the name Germall II | 0.1 g |
| water q.s. | 100.0 g |
| spontaneous pH: 6.6 | |

When applied to washed and roughly dried hair, this milk makes wet hair easier to disentangle and imparts lightness to wet and dried hair.

When applied as a finishing treatment, it makes styling easier and imparts body to the styling.

EXAMPLE 4

A conditioner cream which is not rinsed off is prepared whose composition is as follows:

| | |
|---|---|
| Crosslinked ammonium acrylate/acrylamide copolymer emulsion, sold under the name PAS 5161 by Hoechst | 2.0 g AS as copolymer |
| Polyorganosiloxane containing dimethyl itaconate functional group, of formula: | |

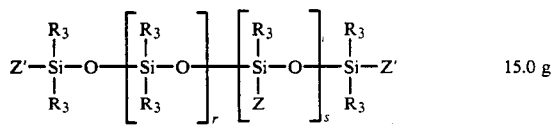

15.0 g in which:
$R_3$ denotes $CH_3$
$Z'$ denotes $OH$
$Z$ is a mixture of radicals:
  $-CH_2-CH(COOCH_3)-CH_2-COOCH_3$
  $-C(CH_3)(COOCH_3)-CH_2-COOCH_3$
$r$ denotes a statistical mean value equal to 40
$s$ denotes a statistical mean value equal to 2 prepared according to Reference Example 2

| | |
|---|---|
| N-(1,3-bis-hydroxymethyl)-2,5-dioxo-4-imidazolidinylurea sold by Sutton under the name Germall II | 0.1 g |
| water q.s. | 100.0 g |
| spontaneous pH: 5.6 | |

This cream is applied to washed and roughly dried hair. After being left on for a few minutes it is rinsed off with water. The hair is easy to disentangle. It has body and is light; the dried hair is gleaming, soft, smooth and easy to style.

EXAMPLE 5

A cream which is applied s a conditioner to be rinsed off is prepared, of the following composition:

| | |
|---|---|
| Crosslinked ammonium acrylate/acrylamide copolymer emulsion, sold under the name PAS 5161 by Hoechst | 1.5 g AS as copolymer |
| PDMS hydroxylated at the end of the chain, in combination with a cyclic PDMS sold by Dow Corning under the name Q2 1401 | 5.0 g |
| Distearyldimethylammonium chloride sold by Hoechst under the name Genamin DSAC | 2.5 g |
| N-(1,3-bis-hydroxymethyl)-2,5-dioxo-4-imidazolinylurea sold by Sutton under the name Germall II | 0.1 g |
| water q.s. | 100.0 g |
| spontaneous pH: 5.7 | |

After the shampooing, this cream is applied to roughly dried hair, is left on for a few minutes and is then rinsed off with water. The wet hair is easy to disentangle and becomes supple and light. The dried hair has body and is gleaming and soft.

EXAMPLE 6

A styling cream is prepared, which is applied to dried hair as a finishing treatment, and whose composition is as follows:

| | |
|---|---|
| Crosslinked ammonium acrylate/acrylamide copolymer emulsion, sold under the name PAS 5161 by Hoechst | 0.3 g AS as copolymer |
| PDMS hydroxylated at the chain end, in combination with a cyclic PDMS, sold by Dow Corning under the name Q2 1401 | 20.0 g |
| N-(1,3-bis-hydroxymethyl)-2,5-dioxo-4-imidazolidinylurea sold by Sutton under the name Germall II | 0.1 g |
| Water q.s. | 100.0 g |
| Spontaneous pH: 6.5 | | this cream is easy to spread on hair; it makes it easy to disentangle and provides sheen, body and good behaviour.

EXAMPLE 7

A shampoo of the following composition is prepared:

| | |
|---|---|
| Crosslinked ammonium acrylate/acrylamide copolymer emulsion, sold under the name PAS 5161 by Hoechst | 0.8 g AS as copolymer |
| Poly(hydroxypropyl ether) nonionic surfactant prepared by condensation, using alkaline catalysis, of 3.5 moles of glycidol with a mixture of $C_{11-14}$ α-diols according to the process described in French Patent No. 2,091,516 | 10.0 g |

Hydroxypropylated polyorganosiloxane of formula:

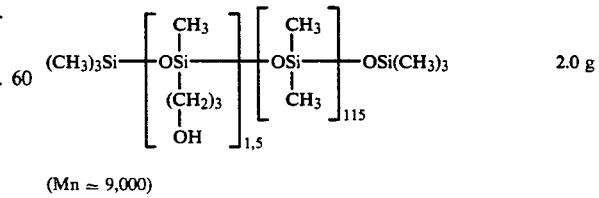

2.0 g (Mn = 9,000)

| | |
|---|---|
| N-(1,3-bis-hydroxymethyl)-2,5-dioxo-4-imidazolidinylurea sold by Sutton under the name Germall II | 0.1 g |
| water q.s. | 100.0 g |

Spontaneous pH: 5.9

This shampoo, with the appearance of an opaque fluid gel, leaves the wet hair light and supple and the dried hair soft and easy to style.

EXAMPLE 8

A hydrating fluid gel for the skin is prepared, of the following composition:

| | |
|---|---|
| Crosslinked ammonium acrylate/acrylamide copolymer emulsion, sold under the name PAS 5161 by Hoechst | 0.5 g AS as copolymer |
| PDMS hydroxylated at the chain end in combination with a cyclic PDMS, sold by Dow Corning under the name Q2 1401 | 15.0 g |
| Glycerine | 5.0 g |
| N-(1,3-bis-hydroxymethyl)-2,5-dioxo-4-imidazolidinylurea sold by Sutton under the name Germall II | 0.1 g |
| Perfume q.s. | |
| Water q.s. | 100.0 g |
| Spontaneous pH: 6.2 | |

This gel imparts much softness and suppleness to the skin.

EXAMPLE 9

A hair-styling composition is prepared, of the following composition:

| | |
|---|---|
| Crosslinked ammonium acrylate/acrylamide copolymer emulsion, sold under the name PAS 5161 by Hoechst | 0.3 g as copolymer |
| PDMS hydroxylated at the chain end, in combination with a cyclic PDMS, sold by Dow Corning under the name Q2 1401 | 20.0 g |
| Polyethyloxazoline of MW 50,000 sold under the name PEOX by Dow Chemical | 3.5 g |
| Preserving agent, colorant, perfume q.s. | |
| Water q.s. | 100.0 g |
| Spontaneous pH: 6 | |

This gel is applied to clean and dried hair. The composition improves hair styling and imparts shape-retention and sheen.

EXAMPLE 10

A hair-styling foam is prepared, which is applied to dried hair as a finishing treatment, whose composition is as follows:

| | |
|---|---|
| Crosslinked ammonium acrylate/acrylamide copolymer emulsion, sold under the name PAS 5161 by Hoechst | 0.2 g AS as copolymer |
| PDMS hydroxylated at the chain end in combination with a cyclic PDMS, sold by Dow Corning under the name Q2 1401 | 13.0 g |
| Ethyl alcohol | 10.0 g |
| Polyvinyl alcohol sold under the name Mowiol 4088 by Hoechst | 0.3 g AS |
| Perfume, preserving agent q.s. | |
| Water q.s. | 100.0 g |
| Triethanolamine q.s. pH = 6.5 | |
| AEROSOL PACKAGING: | |
| Above composition | 90.0 g |
| PROPELLANT: | |
| Ternary mixture of n-butane, >55% isobutane, and propane, sold under the name Aerogaz 3.2 N by Elf Aquitaine | 10.0 g |
| TOTAL | 100.0 g |

This foam can also be applied to washed and roughly dried hair before final drying.

The hair is gleaming, has body, and disentangles easily and is very soft.

EXAMPLE 11

| SUN COMPOSITION | |
|---|---|
| Crosslinked ammonium acrylate/acrylamide copolymer emulsion, sold under the name PAS 5161 by Hoechst | 0.4 g AS as copolymer |
| PDMS hydroxylated at the chain end in combination with a cyclic PDMS, sold under the name Q2 1401 by Dow Corning | 13.0 g |
| 2-Hydroxy-4-methoxybenzophenone sold under the name Uvinul M40 by BASF | 2.0 g |
| 2-Ethylhexyl p-methoxycinnamate sold under the name Parsol MCX by Givaudan | 5.0 g |
| Preserving agent q.s. | |
| Water q.s. | 100.0 g |

EXAMPLE 12

| AFTER-SUN COMPOSITION | |
|---|---|
| Crosslinked ammonium acrylate/acrylamide copolymer emulsion, sold under the name PAS 5161 by Hoechst | 0.4 g AS as copolymer |
| PDMS hyroxylated at the chain end in combination with a cyclic PDMS, sold under the name Q2 1401 by Dow Corning | 13.0 g |
| Glycerine | 3.0 g |
| Sorbitol containing 70% AS | 1.4 g AS |
| Preserving agent q.s. | |
| Water q.s. | 100.0 g |

EXAMPLE 13

An antiinflammatory cream is prepared, of the following composition:

| | |
|---|---|
| Crosslinked ammonium acrylate/acrylamide copolymer emulsion, sold under the name PAS 5161 by Hoechst | 1.5 g AS as copolymer |
| Ammonium salt of glycyrrhizic acid | 0.5 g |
| Polymethylphenylsiloxane sold under the name ABIL AV 1000 by Goldschmidt | 5.0 g |
| Perfume, preserving agent, colorant q.s. | |
| Spontaneous pH: 5.3 | |
| Water q.s. | 100.0 g |

EXAMPLE 14

An antiacne cream is prepared, of the following composition:

| | |
|---|---|
| Crosslinked ammonium acrylate/ acrylamide copolymer emulsion, sold under the name PAS 5161 by Hoechst | 3.0 g AS as copolymer |
| Retinoic acid | 0.1 g |
| PDMS sold under the name 70047V300 by Rhône Poulenc | 20.0 g |
| Perfume, preserving agent, colorant q.s. | |
| Spontaneous pH: 5.4 | |
| Water q.s. | 100.0 g |

In the above examples the molecular weight of the ammonium acrylate/acrylamide polymer before crosslinking is of the order of $5 \times 10^6$.

We claim:

1. An aqueous dispersion intended for the cosmetic treatment of hair or the skin and/or in dermatology, which contains at least an organopolysiloxane and a crosslinked ammonium acrylate/acrylamide copolymer in a cosmetically or physiologically acceptable aqueous medium.

2. Dispersion according to claim 1, wherein the organosiloxane is a volatile silicone which has a boiling point of between 60° C. and 260° C., chosen from:

(i) cyclic silicones containing 3 to 7 and preferably 4 to 5 silicon atoms or cyclocopolymers of the dimethylsiloxane/methylalkylsiloxane type of formula:

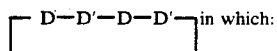 in which:

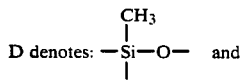

D denotes: and

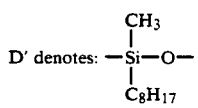

D' denotes:

(ii) linear silicones containing 2 to 9 silicon atoms and having a viscosity lower than or equal to 5 cSt at 25° C.

3. Dispersion according to claim 1, wherein the organopolysiloxane is a nonvolatile silicone chosen from polyalkylsiloxanes, polyarylsiloxanes, polyalkylarylsiloxanes, polyethersiloxane copolymers, modified or otherwise, silicone gums and resins, organomodified polysiloxanes and mixtures thereof.

4. Dispersion according to claim 3, in which the organopolysiloxane is chosen from:

A) polyalkyl($C_1$-$C_{20}$)siloxanes, linear polydimethylsiloxanes containing trimethylsilyl end groups, with a viscosity of 5 to 2,500,000 cSt at 25° C. and preferably 10 to 1,000,000 and linear polydimethylsiloxanes containing trihydroxysilyl end groups;

B) linear and/or branched polydimethylphenylsiloxanes and polydimethyldiphenylsiloxanes with a viscosity of 10 to 50,000 cSt at 25° C.;

C) copolymers of propylene and/or ethylene oxide with a diorganosiloxane;

D) gums with a molecular mass between 200,000 and 1,000,000, employed by themselves or in the form of a mixture in a solvent, which are chosen from the group consisting of the following copolymers:
poly[(dimethylsiloxane)/(methylvinylsiloxane)]
poly[(dimethylsiloxane)/(diphenylsiloxane)]
poly[(dimethylsiloxane)/(phenylmethylsiloxane)]
poly[(dimethylsiloxane)/(diphenylsiloxane)/(methylvinylsiloxane)];

and the following mixtures:
the mixtures made from a polydimethylsiloxane hydroxylated at a chain end and cyclic polydimethylsiloxanes;
the mixtures made from a polydimethylsiloxane gum and a cyclic silicone;
mixtures of two polydimethylsiloxanes of different viscosities;
mixtures of a polydimethylsiloxane with a polyoxyethylenated or polyoxypropylenated side chain and of a cyclic polydimethylsiloxane;

E) organopolysiloxane resins consisting of crosslinked siloxane systems containing the units $R_2SiO_{2/2}$, $RSiO_{3/2}$ or $SiO_{4/2}$, in which R denotes a hydrocarbon group containing 1 to 6 carbon atoms, or a phenyl group.

5. Dispersion according to claim 3, wherein the organopolysiloxane includes in its general structure one or more organofunctional group(s) attached directly to the siloxane chain or attached through the intermediacy of a hydrocarbon radical, and in that it is chosen from polyorganosiloxanes containing:

a) substituted or substituted amine groups;
thiol groups;
c) carboxylate groups;
d) hydroxyalkyl groups, and corresponding to the following formula:

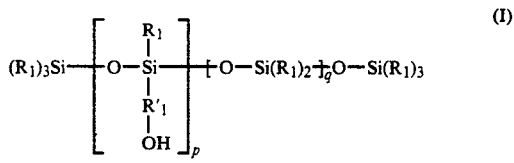

in which:
radicals $R_1$, which are identical or different, are chosen from methyl and phenyl radicals, at least 60 mol % of the radicals $R_1$ being methyl;
the radical $R'_1$ is a $C_2$-$C_{18}$ divalent alkylene hydrocarbon chain unit;
p is between 1 and 30 inclusive;
1 is between 1 and 150 inclusive;
e) alkoxylated groups;
f) acyloxyalkyl groups corresponding to the following formula:

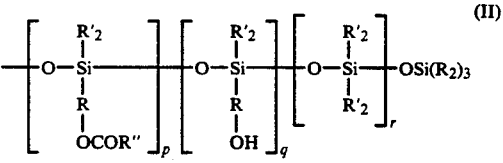

in which:
$R_2$ denotes methyl, phenyl, —$COOR''_2$ or hydroxyl, only one of the $R_2$ per silicon atom may be OH;
$R'_2$ denotes methyl, phenyl, at least 60 mol % of the set of the radicals $R_2$ and $R'_2$ are methyl;
R" denotes $C_8$-$C_{20}$ alkyl or alkenyl;
R denotes a linear or branched $C_2$-$C_{18}$ divalent alkylene hydrocarbon;

r is between 1 and 120 inclusive;
p is between 1 and 30;
q is 0 or smaller than 0.5 p, p+q being between 1 and 30;
it being possible for the polymers of formula (II) to contain

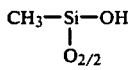

groups in proportions not exceeding 15% of the sum p+q+r;

g) diester groups, in particular dimethyl itaconate, corresponding to the following formula:

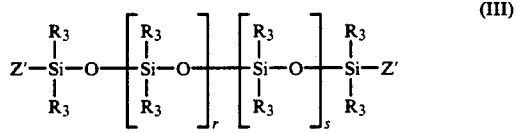

in which:
the radicals $R_3$, which are identical or different, denote a $C_1$-$C_{20}$ alkyl, vinyl, phenyl, 3,3,3-trifluoropropyl or hydroxyl, provided that only one radical $R_3$ may denote OH per silicon atom;
the symbols Z', which are identical or different, denote $R_3$ or Z;
Z is chosen from the groups:
—CH$_2$—CH—(COOR'$_3$)—CH$_2$—COOR'$_3$
—C(CH$_3$)(COOR'$_3$)—CH$_2$—COOR'$_3$
R'$_3$ denotes a $C_1$-$C_{12}$ monovalent saturated hydrocarbon radical, a $C_2$-$C_{12}$ monovalent alkoxyalkyl or a $C_6$-$C_{12}$ aryl, aralkyl or alkylaryl;
r is between 0 and 500 inclusive;
s is between 0 and 50 inclusive;
if s is equal to 0, one of the symbols Z' is Z;
h) quaternary ammonium groups;
i) amphoteric or betainic groups;
j) anionic groups of alkylcarboxylic 2-hydroxyalkyl-sulphonate or 2-hydroxyalkylthiosulphate type.

6. Dispersion according to claim 1, in which the organopolysiloxane is chosen from octamethylcyclotetrasiloxane, decamethylcyclopentasiloxane, linear polyalkylsiloxanes containing trimethylsilyl end groups, mixtures of organosiloxanes and cyclic silicones, dimethyl/trimethylsiloxane resin, polymers of formula (I) in which $R_1$ denotes methyl and $R'_1$ a trimethylene or 2-methyltrimethylene group, polymers of formula (II), in which $R_2$ and $R'_2$ denote methyl, R" a mixture of $C_{16}H_{33}$ and $C_{18}H_{37}$ radicals and R denotes trimethylene or 2-methyltrimethylene; and polymers of formula (III) in which $R_3$ denotes CH$_3$ and Z' denotes OH.

7. Dispersion according to claim 1 which contains an ammonium acrylate/acrylamide (95/5 by weight) copolymer crosslinked with a crosslinking agent containing olefinic polyunsaturation, taken from the group consisting of divinylbenzene, tetraallyloxyethane, diallyl ether, polyallylpolyglyceryl ethers and the allyl ethers of alcohols from the sugar series.

8. Dispersion according to claim 1, which the organopolysiloxane is present in the dispersion in proportions of between 0.5 and 50% by weight and preferably between 1 and 30% by weight and the ammonium acrylate/acrylamide copolymer is present in proportions of between 0.1 and 10% by weight and preferably between 0.1 and 4% by weight relative to the total weight of the dispersion.

9. Dispersion according to claim 1, which additionally contains at least one nonionic emulsifying agent and a mineral oil.

10. Dispersion according to claim 9, in which the nonionic emulsifying agent is chosen from oil-soluble surfactants in which the hydrophile/lipophile ratio is lower than 7.

11. Dispersion according to claim 9, wherein the emulsifying agent consists of a mixture of sorbitan stearate and of a hydrophilic ethoxylated derivative.

12. Dispersion according to claim 9, in which the mineral oil is liquid paraffin.

13. Dispersion according to claim 9, wherein the nonionic emulsifying agent is present in proportions of between 0.01 and 10% by weight and preferably between 0.01 and 0.6% by weight, and the mineral oil is present in proportions of between 0.08 and 6.5% by weight and preferably between 0.08 and 2.5% by weight, the weights being defined in relation to the total weight of the dispersion.

14. Dispersion according to claim 1, wherein the crosslinked ammonium acrylate/acrylamide (95/5 by weight) copolymer is dispersed in a proportion of 30% by weight in a water-in-oil emulsion consisting of 25% by weight of paraffin, 4% by weight of a mixture of sorbitan stearate and of hydrophilic ethoxylated derivative and of 41% by weight of water.

15. Dispersion according to claim 14, in which the water-in-oil emulsion containing the crosslinked ammonium acrylate/acrylamide (95/5 by weight) copolymer is present in the dispersion in proportions such that the concentration of copolymer is between 0.05 and 10% by weight and preferably between 0.1 and 5% by weight of active substance as copolymer relative to the total weight of the dispersion.

16. Composition according to claim 1, which additionally contains adjuvants usually employed in cosmetics, which are chosen from perfumes, colorants, preserving agents, anionic, nonionic, amphoteric or cationic surface-active agents, sequestrants, foam stabilizers, polymers, sunscreens, propellants and cosmetically active substances.

17. Composition according to claim 1, which has a pH of between 3 and 10 and preferably between 5 and 7.

18. Composition according to claim 1, intended for the treatment of hair which is in the form of shampoo, or rinsing product, to be applied before or after shampooing, before or after dyeing or bleaching, before or after permanent waving or straightening, or as unrinsed styling products.

19. Composition according to claim 1, intended for the treatment of the skin which is in the form of a bath or shower product, of a suntanning product, of antisolar composition, of a product for shaving, of a treatment cream or milk or of a perfumed lotion.

20. Process for cosmetic treatment of hair, in which at least one composition such as defined in claim 18 is applied to the latter.

21. Process for cosmetic treatment of the skin, in which a composition such as defined in claim 19 is applied to the latter.

22. Dermatological composition in the form of aqueous dispersion in which the aqueous dispersion is such as defined in claim 1 and contains at least one dermatologically active substance in an effective quantity.

* * * * *